(12) United States Patent
Erickson (10) Patent No.: US 8,543,218 B2
(45) Date of Patent: *Sep. 24, 2013

(54) IMPLANTABLE PULSE GENERATOR COMPRISING MRI CURRENT LIMITING WINDINGS IN HEADER STRUCTURE

(71) Applicant: John H. Erickson, Plano, TX (US)

(72) Inventor: John H. Erickson, Plano, TX (US)

(73) Assignee: Advanced Neuromodulation Sytems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/663,145

(22) Filed: Oct. 29, 2012

(65) Prior Publication Data

US 2013/0116753 A1     May 9, 2013

Related U.S. Application Data

(63) Continuation of application No. 13/540,361, filed on Jul. 2, 2012, now Pat. No. 8,315,715, which is a continuation of application No. 13/356,147, filed on Jan. 23, 2012, now Pat. No. 8,214,055, which is a continuation of application No. 12/109,866, filed on Apr. 25, 2008, now Pat. No. 8,103,347.

(60) Provisional application No. 60/913,908, filed on Apr. 25, 2007.

(51) Int. Cl.
*A61N 1/00*          (2006.01)

(52) U.S. Cl.
USPC .......................................................... 607/65

(58) Field of Classification Search
USPC .......................................................... 607/65
See application file for complete search history.

(56) References Cited

U.S. PATENT DOCUMENTS

| 5,217,010 | A | 6/1993 | Tsitlik et al. | |
|---|---|---|---|---|
| 6,985,775 | B2 | 1/2006 | Reinke et al. | |
| 7,174,219 | B2 | 2/2007 | Wahlstrand et al. | |
| 7,363,090 | B2 | 4/2008 | Halperin et al. | |
| 7,853,324 | B2 * | 12/2010 | Stevenson et al. | 607/2 |
| 8,103,347 | B2 | 1/2012 | Erickson | |
| 8,214,055 | B2 | 7/2012 | Erickson | |
| 2003/0083726 | A1 | 5/2003 | Zeijlemaker et al. | |
| 2003/0144716 | A1 | 7/2003 | Reinke et al. | |
| 2003/0144720 | A1 | 7/2003 | Villaseca et al. | |
| 2005/0027340 | A1 | 2/2005 | Schrom et al. | |

(Continued)

OTHER PUBLICATIONS

Bhachu, Dewinder S., et al., "Implantable Pulse Generators (Pacemakers) and Electrodes: Safety in the Magnetic Resonance Imaging Scanner Environment," Journal of Magnetic Resonance Imaging, 12:201-204 (2000).

(Continued)

*Primary Examiner* — Robert N Wieland (57) ABSTRACT

In one embodiment, a pulse generator for generating electrical stimulation for delivery to a patient, comprises: a hermetically sealed housing containing pulse generating circuitry; a header coupled to the housing for receiving one or more stimulation leads, wherein feedthrough wires are provided to conduct electrical pulses from the pulse generating circuitry to the header; the header comprising a plurality of connectors for electrically connecting to each terminal of the one or more stimulation leads, wherein an inductive winding is disposed around or adjacent to each of the connector structures and is electrically connected between the respective connector structure and a corresponding feedthrough wire to limit MRI induced heating of a respective electrode of the one or more stimulation leads.

8 Claims, 5 Drawing Sheets

(56) References Cited

U.S. PATENT DOCUMENTS

| | | |
|---|---|---|
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2007/0088416 A1 | 4/2007 | Atalar et al. |
| 2007/0112398 A1 | 5/2007 | Stevenson et al. |
| 2007/0185556 A1 | 8/2007 | Williams et al. |
| 2007/0208383 A1 | 9/2007 | Williams |
| 2007/0299490 A1 | 12/2007 | Yang et al. |
| 2008/0009905 A1 | 1/2008 | Zeijlemaker |
| 2008/0033497 A1 | 2/2008 | Bulkes et al. |
| 2008/0116997 A1 | 5/2008 | Dabney et al. |
| 2008/0119919 A1 | 5/2008 | Atalar et al. |
| 2008/0243218 A1 | 10/2008 | Bottomley et al. |
| 2008/0262584 A1 | 10/2008 | Bottomley et al. |
| 2009/0171421 A1 | 7/2009 | Atalar et al. |

OTHER PUBLICATIONS

Buchli R., et al., "Heating Effects of Metallic Implants by MRI Examinations," Magnetic Resonance in Medicine, 7, 255-261 (1988).

Finelli, Daniel, et al."MR Imaging-Related Heating of Deep Brain Stimulation Electrodes: In Vitro Study," Am. J. Neuroradiol, 23:1795-1802, Nov./Dec. 2002.

Ho, Henry S., "Safety of Metallic Implants in Magnetic Resonance Imaging," Journal of Magnetic Resonance Imaging, 14: 472-477 (2001).

* cited by examiner

IMPLANTABLE PULSE GENERATOR COMPRISING MRI CURRENT LIMITING WINDINGS IN HEADER STRUCTURE

CROSS-REFERENCE TO RELATED APPLICATIONS

This application is a continuation of U.S. application Ser. No. 13/540,361, filed Jul. 2, 2012, now U.S. Pat. No. 8,315,715, which is a continuation of U.S. application Ser. No. 13/356,147, filed Jan. 23, 2012, now U.S. Pat. No. 8,214,055, which is a continuation of U.S. application Ser. No. 12/109,866, filed Apr. 25, 2008, now U.S. Pat. No. 8,103,347, which claims the benefit of U.S. Provisional Application No. 60/913,908, filed Apr. 25, 2007.

BACKGROUND

The present application is generally related to adapting the electrical contacts within the header of a pulse generator to mitigate or limit current induced in an MRI environment.

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses. The pulse generator is usually implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the nerve tissue.

There are concerns related to the compatibility of neurostimulation systems with magnetic resonance imaging (MRI). MRI generates cross-sectional images of the human body by using nuclear magnetic resonance (NMR). The MRI process begins with positioning the patient in a strong, uniform magnetic field. The uniform magnetic field polarizes the nuclear magnetic moments of atomic nuclei by forcing their spins into one of two possible orientations. Then an appropriately polarized pulsed RF field, applied at a resonant frequency, forces spin transitions between the two orientations. Energy is imparted into the nuclei during the spin transitions. The imparted energy is radiated from the nuclei as the nuclei "relax" to their previous magnetic state. The radiated energy is received by a receiving coil and processed to determine the characteristics of the tissue from which the radiated energy originated to generate the intra-body images.

Neurostimulation systems are designated as being contraindicated for MRI, because the time-varying magnetic RF field causes the induction of current which, in turn, can cause significant heating of patient tissue due to the presence of metal in various system components. The induced current can be "eddy current" and/or current caused by the "antenna effect."

Figure 1:
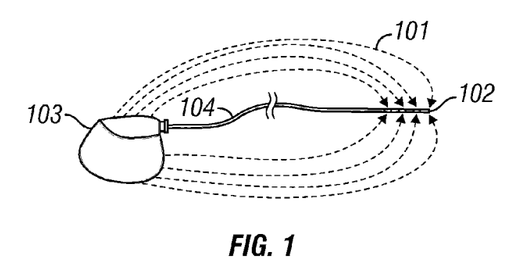
FIG. 1 depicts closed-paths of current induced by the time-varying magnetic RF field of an MRI system.

"Eddy current" refers to current caused by the change in magnetic flux due to the time-varying RF magnetic field across an area bounding conductive material (i.e., patient tissue). As shown in a simplified form in FIG. 1, the time-varying magnetic RF field induces current within the tissue of a patient that flows in closed-paths. When conventional pulse generator 103 and conventional implantable lead 104 are placed within tissue in which eddy currents are present, implantable lead 104 and pulse generator 103 provide a low impedance path for the flow of current. As depicted in FIG. 1, electrode 102 provides a conductive surface that is adjacent to current path 101. Electrode 102 is coupled to pulse generator 103 through a wire conductor (not shown) within implantable lead 104. The hermetically sealed metallic housing (the "can") of pulse generator 103 also provides a conductive surface in the tissue in which eddy currents are present. Thus, current can flow from the tissue through electrode 102 and out the metallic housing of pulse generator 103. Because of the low impedance path and the relatively small surface area of electrode 102, the current density in the patient tissue adjacent to electrode 102 can be relatively high. Accordingly, resistive heating of the tissue adjacent to electrode 102 can be high and can cause significant tissue damage.

Also, the "antenna effect" can cause current to be induced which can result in undesired heating of tissue. Specifically, depending upon the length of the stimulation lead and its orientation relative to the time-varying magnetic RF field, the wire conductors of the stimulation lead can each function as an antenna and a resonant standing wave can be developed in each wire. A relatively large potential difference can result from the standing wave thereby causing relatively high current density and, hence, heating of tissue adjacent to the electrodes of the stimulation lead.

A number of proposals have been published that attempt to mitigate MRI induced current in a stimulation system. For example, it has been proposed to couple each wire conductor of a stimulation lead to an inductor. The frequency-dependent characteristic of the inductor tends to limit the higher frequency MRI currents. The typical approach to implement the inductor involves wrapping a wire multiple times around the stimulation lead. Additionally, the lead can be specifically adapted to accommodate the wire windings for the inductor. For example, "bobbin" structures can be placed over the stimulation lead to accommodate the wire windings.

SUMMARY

In one embodiment, a pulse generator for generating electrical stimulation for delivery to a patient, comprises: a hermetically sealed housing containing pulse generating circuitry; a header coupled to the housing for receiving one or more stimulation leads, wherein feedthrough wires are provided to conduct electrical pulses from the pulse generating circuitry to the header; the header comprising a plurality of connectors for electrically connecting to each terminal of the one or more stimulation leads, wherein an inductive winding is disposed around or adjacent to each of the connector structures and is electrically connected between the respective connector structure and a corresponding feedthrough wire to limit MRI induced heating of a respective electrode of the one or more stimulation leads.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Stimulation leads are typically connected to a pulse generator through a "header" that contains various connector structures. The connector structures are contained within a suitable housing of epoxy and/or various polymers. The connector structures mechanically and electrically typically couple to the terminals of the stimulation lead(s). Also, the connector structures are electrically connected to feedthrough wires. The feedthrough wires extend into the hermetically sealed metallic housing that contains the pulse generating circuitry. The term "header" is used in the art, because the header is usually disposed on an upper surface of the metallic housing (although the header can be disposed anywhere on the device as long as it is reasonably accessible).

Figure 2A:
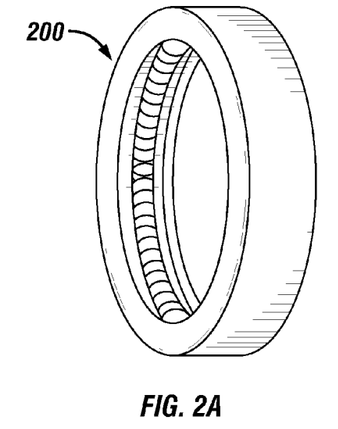
FIG. 2A shows a conventional electrical connector.

FIG. 2A shows a conventional electrical connector, which would be located in the header of a pulse generator and is used to electrically couple a terminal of the stimulation lead with a respective feedthrough wire that is, in turn, coupled to the pulse generation circuitry of the pulse generator. As shown in FIG. 2A, connector or contact 200 (which is typically one of several connectors disposed within a header) has a cylindrical band having an inner groove bounded by a lower lip and an upper lip. The groove bounded by the upper and lower lip in this instance contains a coiled spring, which contacts (electrically couples) to a corresponding terminal of the implantable lead when the lead passes through the connector. Such conventional electrical connectors are commercially available (e.g., from Bal Seal Engineering, Inc. of Foothill Ranch, Calif.).

Figure 2B:
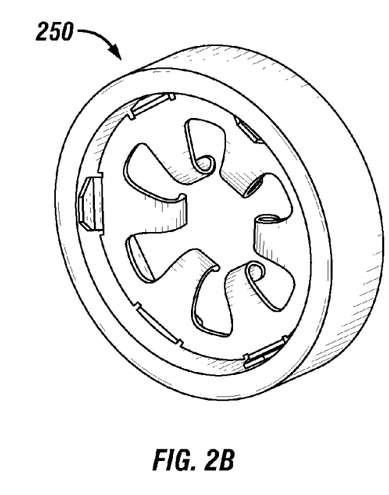
FIG. 2B depicts another electrical connector in which substantially planar conductive disk is utilized within a metallic band in lieu of a spring.

Other designs for electrical contacts for use in the header of a pulse generator are known. For example, FIG. 2B depicts connector 250 in which a substantially planar conductive disk is utilized within a band in lieu of the coiled spring which is described in greater detail in U.S. Patent Application Publication No. 20050107859, entitled "System and method of establishing an electrical connection between an implanted lead and an electrical contact," which is incorporated herein by reference (now abandoned). The conductive disk comprises multiple arcuate tabs that mechanically and electrically couple to the terminals of a lead.

Figure 3:
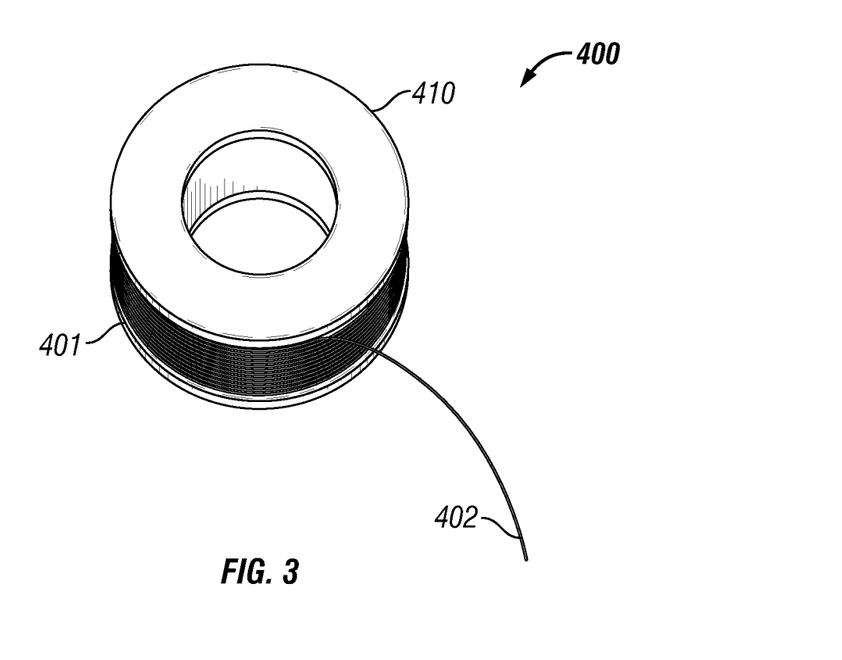
FIG. 3 depicts assembly for implementing an electrical connector or contact within a header of a pulse generator according to one representative embodiment.
Figure 4:
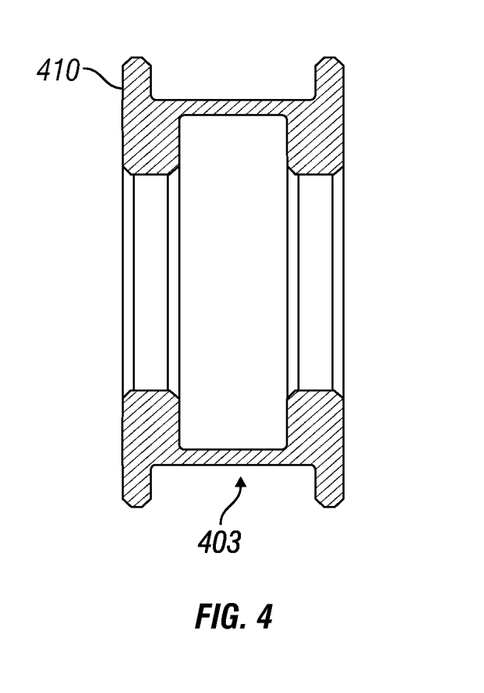
FIG. 4 depicts an annular conductive structure for use within an electrical connector according to one representative embodiment.

FIG. 3 depicts assembly 400 for implementing an electrical connector or contact within a header of a pulse generator according to one representative embodiment. Assembly 400 comprises wire 401 which is wound about groove 403 on the outside diameter of ring 410 (shown in isolation in FIG. 4). Any suitable conductive material can be utilized for wire 401 such as silver-cored MP35N or stainless steel as examples. An insulative sheath is preferably provided that surrounds the conductive material (except where at the ends of wire 401 where connected to other conductive elements). One end of the winding is electrically coupled to the housing to establish an electrical connection through the ring 410 (and the associated coiled spring) to a terminal of the stimulation lead. The other end 402 of wire 401 is electrically coupled to the feedthrough wire (not shown). The feedthrough wire is the wire that extends from the header into the hermetically sealed "can" (the metallic housing that contains the pulse generation circuitry) and that is coupled to the switch matrix of the pulse generation circuitry. The electrical coupling can be accomplished by welding the ends of wire 401 to ring 410 and the feedthrough wire respectively.

The multiple windings of wire 401 about ring 410 provide inductance that is utilized to suppress MRI induced current. Specifically, the inductance of the winding provides an impedance that limits the current that can be passed from the "can" of the pulse generator through the feedthrough wires to the electrodes of the stimulation lead. The number of turns of the wire 401 and the material for wire 401 can be selected to achieve an impedance at stimulation frequencies (e.g., below 5000 Hz) that is relatively low and provides significant attenuation at MRI frequencies (e.g., 64 MHz).

The inductance of the winding is related the value of $\mu_0 N^2 A/L$, where $\mu$ is the electrical permeability of free space, N is the number of turns of the winding, A is the cross section area bounded by the windings, and L is the length of windings. The actual inductance will vary from the calculated value to some degree due to the inclusion of conductive material within ring of the connector upon which windings of wire 401 are wrapped. The actual inductance of a winding of wire 401 about a connector can be readily measured utilizing suitable electronic equipment (e.g., a vector network analyzer). Also, to the extent sufficient attenuation of MRI is achieved, it is preferred to minimize the length of the winding of wire 401, because the resistance of the wire 401 is related to its length.

There are a number of advantages to disposing wire windings in the header of a pulse generator rather than within or on the lead itself. One particular advantage is the diameter of the winding is not unduly limited by the diameter of the stimulation lead. Specifically, stimulation leads usually possess relatively minimal outside diameters to facilitate their implantation within a patient. Accordingly, windings applied to the lead are somewhat cumbersome to produce. Also, the use of "bobbins" or other structures on stimulation leads to facilitate the winding process increases the outside diameter and generally prevents an isodiametric profile for the lead. Additionally, the use of the wire windings in the header of a pulse generator reduces the number of windings necessary to achieve the same amount of inductance as would be required for a smaller diameter. Also, lower stray capacitance is achieved.

Figure 5:
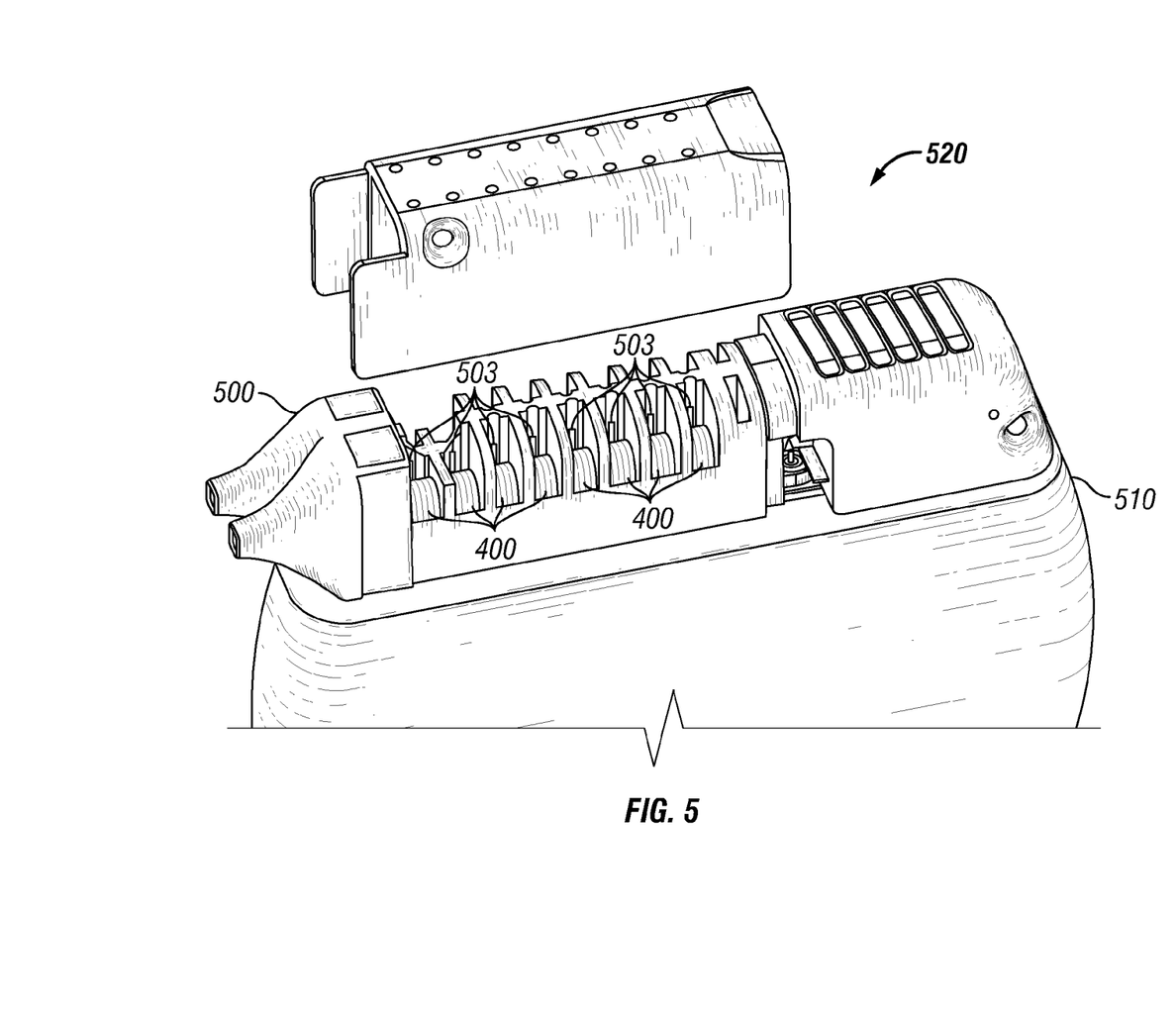
FIG. 5 depicts a pulse generator with a header containing multiple electrical connectors according to another representative embodiment.

FIG. 5 depicts pulse generator 520 with multiple connectors 400 within header 500 according to one representative embodiment. Pulse generator 520 comprises metallic housing 510 that contains the pulse generating circuitry, control circuitry, communication circuitry, battery, etc. Feedthrough wires 503 originate within metallic housing 510 and extend into header 500 to provide respective electrical connections to the pulse generating circuitry within metallic housing 510. Connectors 400 are held in place within respective recesses within the polymer structure of header 500. Connectors 400 are electrically coupled to respective feedthrough wires 503 to enable electrical connection with respective terminals of stimulation lead. The inductive windings of connectors 400 limit MRI induced current from flowing through connectors 400 thereby mitigating MRI induced heating of patient tissue.

Figure 6:
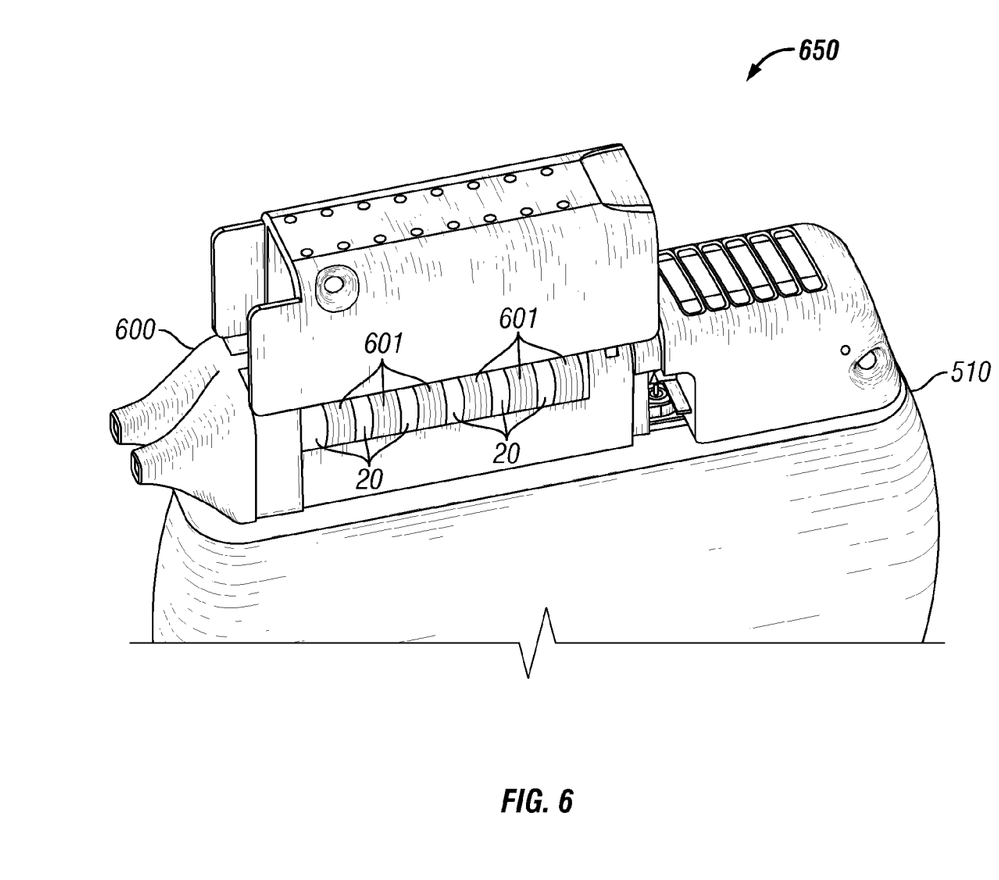
FIG. 6 depicts a pulse generator header where windings are disposed on spacer structure according to an alternative embodiment.
Figure 7:
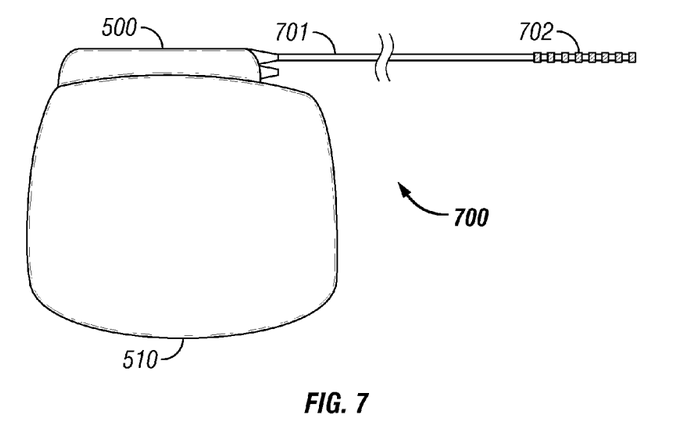
FIG. 7 depicts a stimulation system according to one representative embodiment.

In an alternative embodiment as shown in FIG. 6, header 600 of pulse generator 650 disposes the windings 401 on spacer structures 601 (which are electrically non-conductive) that are disposed between conventional electrical connectors 20. FIG. 7 depicts stimulation system 700 according to one representative embodiment. Stimulation system 700 comprises metallic housing 510 coupled to header 500 that is adapted to suppress or mitigate MRI induced currents by disposing inductive windings between electrodes 702 of stimulation lead 701 and the metallic housing 510 of the system.

The pulse generation circuitry (not shown) within metallic housing 510 can be any suitable pulse generation circuitry now known or later developed. The pulse generating circuitry can be voltage or current pulse generating circuitry. Also, the pulse generating circuitry can include one pulse source or multiple pulse sources that independently produce output pulses. An examples of pulse generating circuitry may be found in U.S. Patent Application Publication No. 20060170486, entitled "Pulse generator having an efficient fractional voltage converter and method of use," which is incorporated herein by reference (now abandoned). Also, the pulse generator can be adapted for any particular medical application such as for spinal cord stimulation, peripheral nerve stimulation, deep brain stimulation, cortical stimulation, cardiac pacing or defibrillation, etc. Lead 701 can be any suitable stimulation lead that is capable of being received within a header of a stimulation system either now existing or later developed. Lead 701 can be a percutaneous lead or a paddle-style lead. Suitable commercially available leads include Axxess® and Lamitrode® leads available from Advanced Neuromodulation Systems, Inc. of Plano, Tex.

Figure 8:
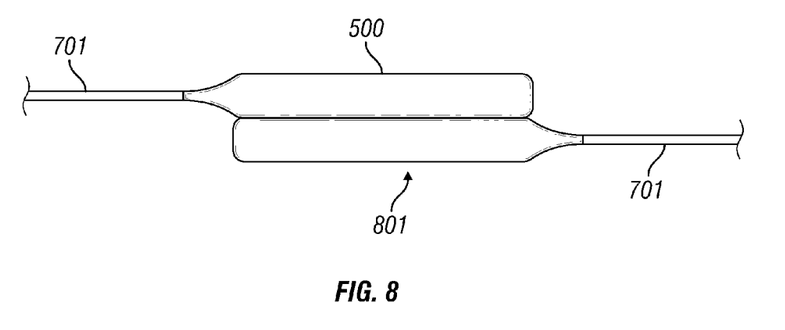
FIG. 8 depicts a header adapted for an extension connector that is utilized to electrically couple two leads according to one representative embodiment.

In another alternative embodiment, header 500 can be disposed within lead extension connector 801 that is utilized to electrically couple two leads 701 as shown in FIG. 8. Extension connector 801 includes an implantable housing that has a first and second aperture for receiving electrodes of a first stimulation lead and for receiving terminals of a second stimulation lead. A first plurality of electrical connectors are disposed within the first aperture for electrically connecting to the electrodes of the first stimulation lead. A second plurality of electrical connectors are disposed within the first aperture for electrically connecting to the electrodes of the first stimulation lead. Also, a plurality of connector wires are provided for electrically coupling the first plurality of electrical connectors with the second plurality of electrical connectors. MRI induced current is suppressed or mitigated by utilizing windings according to representative embodiments. For example, at least one of the first and second plurality of electrical connectors comprises a respective inductive winding disposed around or adjacent to each of the electrical connectors. Each inductive winding is electrically disposed between the respective electrical connector and a corresponding connector wire to limit MRI induced current. The inductive windings are preferably welded between respective connectors wires and electrical connectors.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed:

1. A method of providing electrical stimulation to a patient as a medical therapy using an implantable pulse generator and a stimulation lead, the method comprising:

providing a connector implant device, the connector implant device comprising (i) an implantable housing, (ii) an aperture within the housing for receiving a portion of the stimulation lead, (iii) a plurality of electrical connectors within the aperture for electrically connecting to the electrical contacts of the stimulation lead, wherein each of the plurality of electrical connectors comprises a respective outer surface, and (iv) a respective inductive winding disposed around the outer surface of each of the electrical connectors, wherein the respective inductive winding is adapted to limit MRI induced current flow via the stimulation lead when disposed in an operating MRI system;

inserting the stimulation lead into the connector implant device with one or more electrodes of the stimulation lead adjacent to electrically excitable tissue of the patient;

connecting the implantable pulse generator to the stimulation lead through the connector implant device;

generating stimulation pulses by the implantable pulse generator;

delivering the generated stimulation pulses to the patient using the one or more electrodes stimulation lead to treat one or more medical conditions of the patient; and filtering MRI induced current in the connector implant device when the stimulation lead is disposed in an operating MRI system.

2. The method of claim 1 wherein each outer band of the plurality of electrical connectors comprises a groove on an outside diameter of the band to accommodate its corresponding inductive winding.

3. The method of claim 2 wherein each electrical connector comprises a coiled spring within an interior of the outer band, wherein the coiled spring is adapted to electrically engage an electrical contact of the stimulation lead.

4. The method of claim 1 wherein the stimulation lead is a paddle lead with electrodes on a substantially flat distal end of the stimulation lead.

5. The method of claim 1 wherein the stimulation lead comprises a substantially round cross-sectional profile.

6. The method of claim 1 wherein each inductive winding is welded to the outer band of its corresponding electrical connector.

7. The method of claim 1 wherein each inductive winding is adapted to substantially limit current near 64 MHz.

8. The method of claim 1 wherein each inductive winding is adapted to substantially pass current under 5000 Hz.

* * * * *